United States Patent [19]

Oishi et al.

[11] Patent Number: 5,763,877
[45] Date of Patent: Jun. 9, 1998

[54] ANALYZER USING PLASMA AND ANALYSIS METHOD USING PLASMA, INTERFACE USED FOR THE SAME AND SAMPLE INTRODUCING COMPONENT USED FOR THE SAME

[75] Inventors: Konosuke Oishi, Mito; Masamichi Tsukada, Minori-machi; Toyoharu Okumoto; Takashi Iino, both of Hitachinaka, all of Japan

[73] Assignee: Hitachi, Ltd., Tokyo, Japan

[21] Appl. No.: 715,587

[22] Filed: Sep. 18, 1996

[30] Foreign Application Priority Data

Sep. 29, 1995 [JP] Japan .................................. 7-252409

[51] Int. Cl.$^6$ .......................... H01J 49/10; G01N 21/73
[52] U.S. Cl. ................. 250/288; 356/316; 315/111.51; 219/121.52
[58] Field of Search .......................... 250/288; 356/316; 315/111.51; 219/121.52

[56] References Cited

U.S. PATENT DOCUMENTS

| 4,448,246 | 5/1984 | Meyer et al. | 356/316 |
| 5,200,595 | 4/1993 | Boulos et al. | 315/111.51 |
| 5,400,665 | 3/1995 | Zhu et al. | 250/288 |

FOREIGN PATENT DOCUMENTS

| A-3905303 | 8/1989 | Germany . |
| 1-309300 | 12/1989 | Japan . |
| 1309300A | 12/1989 | Japan . |

OTHER PUBLICATIONS

Patent Abstracts of Japan, vol. '96, No. 001, & JP-A-005555 (Hitachi, Ltd.), Jan. 12, 1996.

Patent Abstracts of Japan, vol. 014, No. 108 (E-0896), Feb. 27, 1990 & JP-A-01 309300 (Hitachi, Ltd.), Dec. 13, 1989 & DE-A-39 05 303 (Hitachi), Aug. 31, 1989.

*Primary Examiner*—Jack I. Berman
*Attorney, Agent, or Firm*—Kenyon & Kenyon

[57] ABSTRACT

In an analyzer in which plasma is generated, a sample is supplied to the plasma though an aerosol guide tube and analyzed by a quadrapole mass filter, the top end portion of the aerosol guide tube is made of sapphire.

12 Claims, 4 Drawing Sheets

ANALYZER USING PLASMA AND ANALYSIS METHOD USING PLASMA, INTERFACE USED FOR THE SAME AND SAMPLE INTRODUCING COMPONENT USED FOR THE SAME

BACKGROUND OF THE INVENTION

The present invention relates to an analyzer using plasma and an analysis method using plasma.

In recent years, there is a growing need to analyze trace elements. For example, there is a need to analyze trace, contaminative elements on a silicon wafer in semiconductor electronic materials, or trace, toxic heavy metals contained in environmental water such as water in a lake. For analysis of such trace elements, analysis using plasma is effective. That is, plasma is generated first, and a sample is supplied to the plasma to be analyzed. Such an analyzer is disclosed in, for example, Japanese Patent Application Laid-Open No. 1-309300.

In the analyzer using plasma, a sample is supplied to the plasma through a passage. The inventors of the present invention discovered in the course of development based on experiments that the analyzer using plasma had more noise compared to the other analytical methods. It was clarified that the surface of the sample passage dissolves as an impurity due to high temperature of the plasma, becomes the noise in analysis data. The mixed noise can be reduced by decreasing the plasma temperature, but there arises a problem in that the analysis cannot be sufficiently performed. The affect can be reduced by setting the plasma apart from the sample passage, but there arises a problem in that the sample cannot diffuse into the plasma and consequently analysis cannot be sufficiently performed.

SUMMARY OF THE OF THE INVENTION

The present invention improves analyzing accuracy in an analysis using plasma.

According to the present invention, in analyzing a sample by supplying the sample to plasma through an introducing passage, the introducing passage is constructed so that at least a portion of the introducing passage in the plasma side has a withstanding temperature higher than a withstanding temperature of a portion of said introducing passage in an inlet side.

By constructing the introducing passage as described above, dissolution can be suppressed in the portion of the introducing passage near the plasma side because this portion has a high withstanding temperature, and accordingly the analysis accuracy can be improved.

Further, according to the present invention, in analyzing a sample by supplying the sample to plasma through an introducing passage, at least a portion of the introducing passage in the range of 1.5 mm to 3.0 mm from the end surface in the plasma side is designed so as to have a proper heat resistant structure.

The inventors of the present invention noticed that effect of the plasma concentrated on a portion of the introducing passage in the range of 1.5 mm to 3.0 mm from the end surface in the plasma side. Therefore, the portion was designed so as to have a proper heat resistant structure. By doing so, the effect can be suppressed, and accordingly the analysis accuracy can be improved.

Furthermore, in analyzing a sample by supplying the sample to plasma through an introducing passage, the introducing passage is constructed so as to essentially withstand a temperature corresponding to approximately 1300 W.

That is, if the plasma is in a temperature corresponding to approximately 1300 W, the analysis can be performed sufficiently. Since the introducing passage is not affected by the plasma, the analysis accuracy can be improved. dr

DETAILED DESCRIPTION OF THE PREFERRED EMBODIMENTS

Embodiments of the present invention will be described below, referring to the accompanying drawings.

Figure 2:
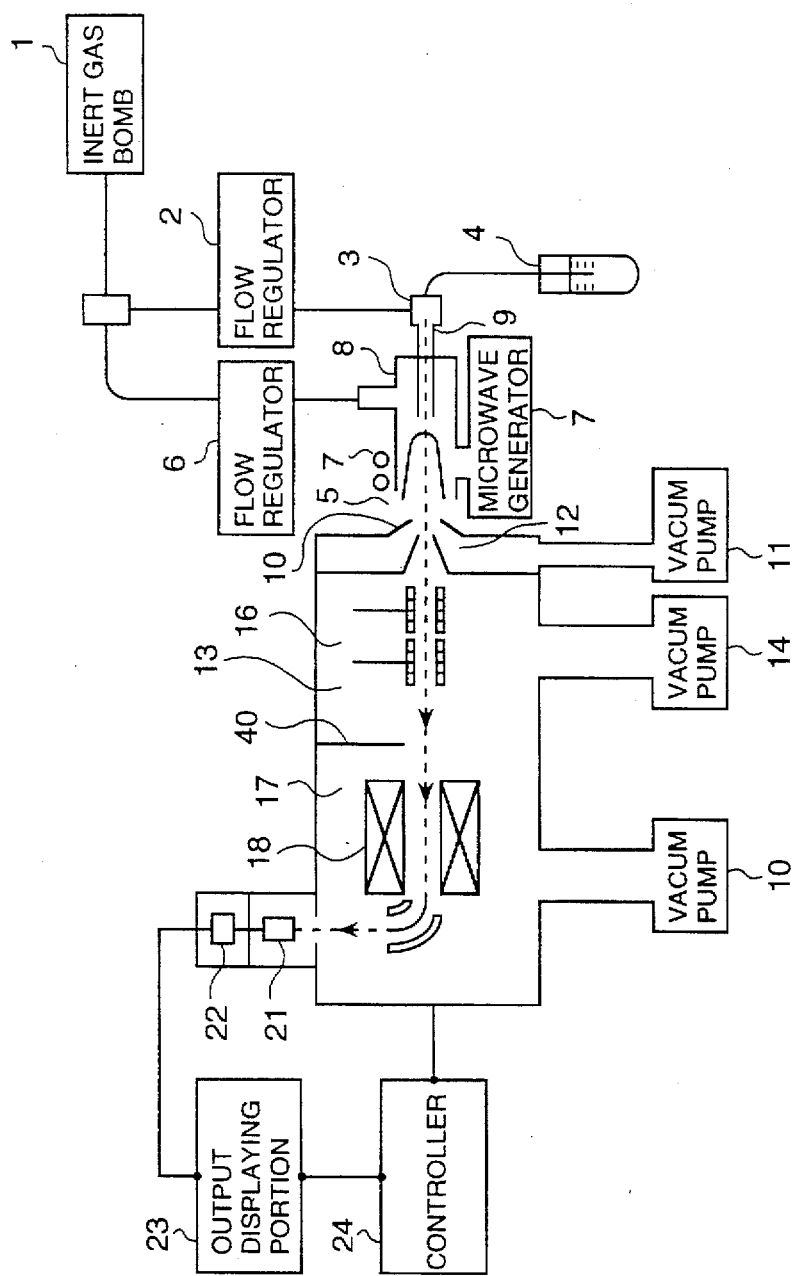
FIG. 2 is a view showing the overall construction of an analyzer.
Figure 3:
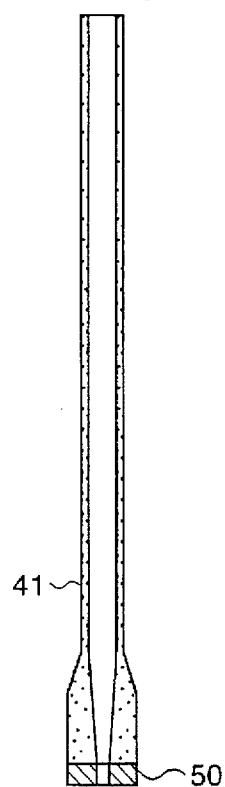
FIG. 3 is a view showing the detailed construction of an aerosol guide tube.

FIG. 2 shows the overall construction of a mass analyzer. An inert plasma gas such as argon or nitrogen is supplied from an inert gas cylinder 1 to each of a nebulizer 3 and a torch tube 8 through flow regulators 2, 6. The inert gas supplied to the nebulizer 3 acts as a carrier gas, and the nebulizer 3 sucks and atomizes a liquid sample 4 through the carrier gas. The atomized sample 4 is introduced into plasma 5 in the form of aerosol. The plasma 5 is generated by ionization through plasma gas discharge by energy of microwave (2.45 GHz) supplied to a microwave generator 7. The plasma 5 may be generated by energy generated by a high frequency coil. The plasma 5 is in contact with a cone-shaped surface having a cooled periphery and a conductive metal sampling cone 10 having an opening in the vertex, and ion flow is sucked and extracted through the opening of the sampling cone the back surface of which is depressurized. The sampling cone 10 broadens toward its mouth, as shown in the figure. The extracted ion flow is further in contact with a cone-shaped skimmer cone 12 having a small hole in the vertex, and the ion flow is sucked and extracted by a vacuum chamber 13 through the small hole of the skimmer cone the back surface of which is further depressurized. The skimmer cone 12 also broadens toward its mouth, as shown in the figure. An electrostatic lens 16 is provided in the vacuum chamber 13, and the ion flow is converged to an opening of a separating wall 40 by the electrostatic lens and then enters into a vacuum chamber 17.

Then, the ion flow enters into a quadrapole mass filter 18 to be mass-analyzed. That is, ions having an objective mass number (m/z) are selected. The ions having the selected mass number pass through a deflection lens 20 and enter in an ion detector 21 to be detected. The detected ions are counted by a pulse amplifier 22 and the counted result is displayed in an output display 23. A controller 24 automatically controls the whole mass analyzer as a system.

The plasma is generated under an atmospheric pressure, and a vacuum pump 19 evacuates the vacuum chamber 17 for mass-analyzing so as to maintain the vacuum chamber at $10^{-4}$ Pa ($10^{-6}$ Torr) or higher vacuum.

The torch 7 and its periphery will be described below in detail, referring to FIG. 1. The microwave generator 7 is connected to a casing 39 through a flange 31. Microwaves generated in the microwave generator 7 are introduced through a microwave introducing port 22 to produce a strong high frequency electric field near an inner conductor 33 and an outer conductor 34. Nitrogen gas or argon gas (approximately 13 l/min) is introduced through a gas inlet 38 of a discharge tube 35, and flows between the discharge tube 35 and an aerosol guide tube 41 to be guided to the top end portion of the aerosol guide tube 41. The nitrogen gas (argon gas) arriving at the top end portion of the aerosol guide tube 41 is discharged by the high frequency electric field to form high temperature plasma.

On the other hand, nitrogen gas or argon gas (approximately 1 l/mim) is mixed with an aerosol sample and introduced through a gas inlet 36. The mixed sample is guided to the top end portion of the aerosol guide tube through the inside of the aerosol guide tube 41.

The top end portion of the aerosol guide tube 41 is filled with plasma. Therefore, for the aerosol guide tube 41, it is necessary to select a material which is easily shapable and comparatively heat-resistant and, at the same time, small dielectric loss for microwave having frequency of 2.45 GHz. Therefore, quartz is used as a material satisfying these conditions. In the aerosol guide tube 41, it is known that when the microwave output is increased to, for example, 1300 W, emission spectrum of silicon, constituent element of the aerosol guide tube, or silicon ions are emitted from the plasma 10. In other words, a small amount of the surface of the end portion of the aerosol guide tube 41 is melted and evaporated by the plasma, and carried into the plasma 10 with the nitrogen or argon gas. Therefore, the top end portion 42 of the aerosol guide tube 41 is made of a material which is high heat-resistant and small dielectric loss for microwave. That is, a thin plate (1.5 mm to 3.0 mm) made of high purity sapphire ($Al_2O_3$) is employed.

The aerosol sample is dissociated into atoms by the high temperature plasma to emit a spectrum inherent in the atom, and the atoms are ionized to produce ions. Since the amount of the ions is proportional to the amount of metallic element contained in the aerosol, the quantitative analysis is performed by measuring the ions. Similarly, it is no need to say that since the light intensity of atom spectrum is also proportional to the amount of metallic element contained in the aerosol, the quantitative analysis can be performed by measuring the light intensity of atom spectrum.

If even a very small amount of the aerosol guide tube is dissolved, vapor of the dissolved element becomes an impurity in element analysis to decrease the detectable limit of element in the analysis. However, in the present invention, since the top end portion of the aerosol guide tube 41 is made of sapphire, such a disadvantage can be eliminated.

Figure 1:
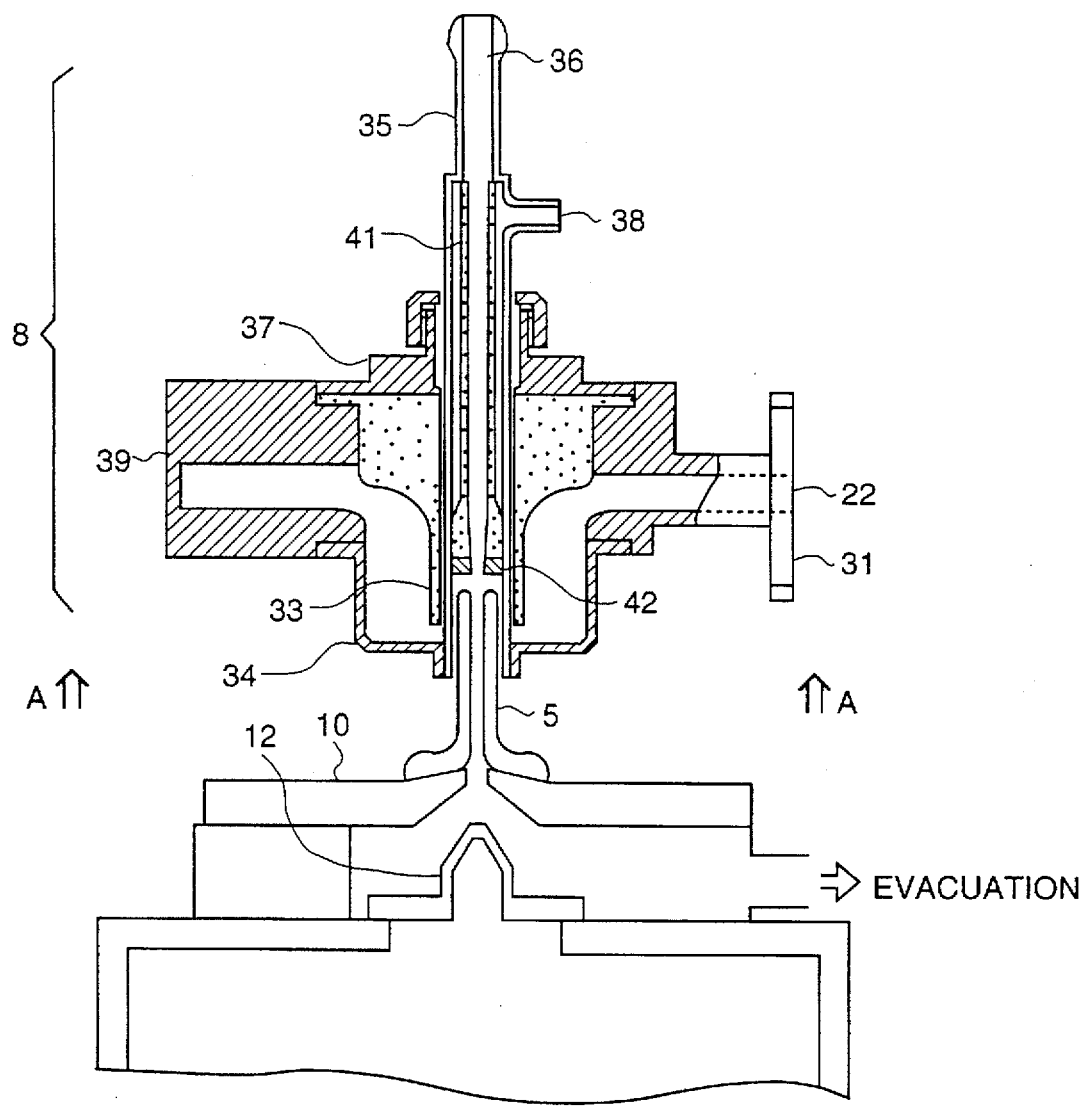
FIG. 1 is a view showing the detailed construction around plasma.

In a case where the top end portion of the aerosol guide tube 41 is made of quartz instead of sapphire, the top end portion (ejecting port) of the aerosol guide tube 41 is set apart from the right hand end of the plasma 10 (the discharge tube 5 is drawn toward the right hand side to the cylindrical inner conductor 3 in FIG. 1) in order to prevent the surface of the top end portion of the aerosol guide tube from dissolving. In that case, the linear velocity of the ejected sample aerosol is decreased and cannot enter into the central portion of the hard plasma 10 (atmospheric pressure plasma having temperature of approximately 5400 K has a characteristic to repulses an ordinary temperature gas flow). That is, in order to efficiently introduce a sample aerosol into the central portion of the hard plasma 10, the top end portion, ejecting port, of the aerosol guide tube cannot be set apart from the plasma 10 so much. In the embodiment, since the top end portion of the aerosol guide tube 41 can be set near the plasma 10, such a disadvantage can be eliminated.

Figure 4:
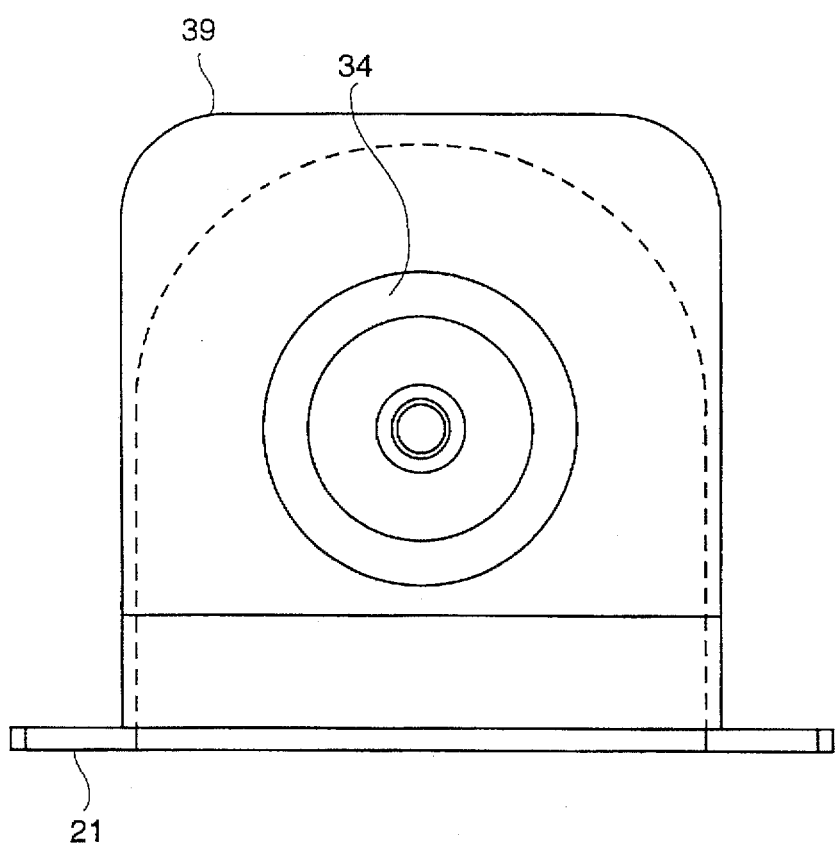
FIG. 4 is a view showing the outward appearance of a torch tube.

FIG. 4 shows the outward appearance of the torch tube seeing from the direction of A—A in FIG. 1.

Figure 5:
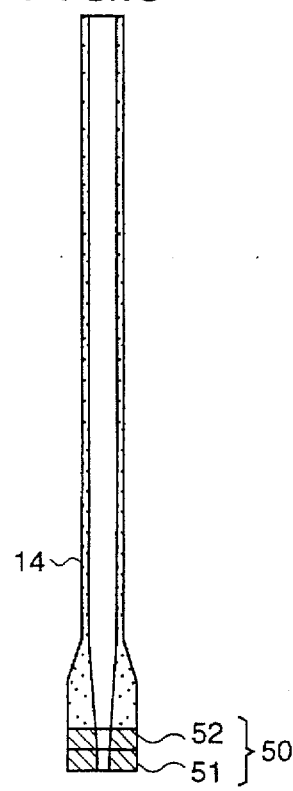
FIG. 5 is a view showing a second embodiment in accordance with the present invention.

A second embodiment will be described below, referring to FIG. 5. Description will be made only to different points of this embodiment from the first embodiment, and the others will be omitted.

In the second embodiment, the top end portion 50 of the aerosol guide tube 41 is made of alumina. Silicon carbide or silicon nitride may be used instead of alumina. However, all portion of the aerosol guide tube cannot be made of alumina. Alumina has very weak thermal shock resistance due to radiation heating of the high temperature plasma, and destruction (intra-granular destruction:cracks) occurs inside alumina crystal grains. According to an experiment, position of crack occurrence is in the range of 1.5 mm to 3.0 mm from the left end surface of the aerosol guide tube 41. Therefore, a material which has a withstanding temperature higher than alumina and, at the same time, a low dielectric loss for microwave having frequency of 2.45 GHz, for example, sapphire is employed so as to be connected to the tip of the aerosol guide tube 41. The aerosol guide tube 41 is constructed by bonding a sapphire plate 52 having a thickness of 1.5 mm to 3 mm to the surface of the gas exit made of alumina.

However, a thermal stress moderating member is inserted between the alumina member 52 and the sapphire member 51 to prevent delaminating due to thermal stress.

According to an experiment conducted by the inventors of the present invention, it was confirmed that, in the discharge tube 5 having the aerosol guide tube 14, the surface in the gas exit portion did not dissolved against the plasma generated by a microwave having an output of 1300 W to 1500 W, and cracks due to thermal shock load did not occur.

As having been described above, according to the present invention, it is possible to perform a high accurate analysis.

What is claimed is:

1. An analyzer using plasma comprising:
   a plasma generator;
   an introducing passage for supplying a sample to said plasma;
   an analyzing unit for analyzing said sample supplied to the plasma;
   wherein at least a portion of said introducing passage in a plasma side is constructed so as to have a withstanding temperature higher than a withstanding temperature of a portion of said introducing passage in an inlet side; and
   a thermal stress moderating member inserted between said portion of said introducing passage having the higher withstanding temperature and the other portion of said introducing passage.

2. The analyzer using plasma according to claim 1, wherein said portion of said introducing passage having the higher withstanding temperature is made of sapphire.

3. The analyzer using plasma according to claim 1, wherein said portion of said introducing passage having the higher withstanding temperature is made of alumina.

4. The analyzer using plasma according to claim 1, wherein said portion of said introducing passage having the higher withstanding temperature is made of any one of silicon carbide and silicon nitride.

5. The analyzer using plasma according to claim 1, wherein said introducing passage is made of quartz.

6. The analyzer using plasma according to claim 1, wherein said portion of said introducing passage having the higher withstanding temperature has a thickness not thicker than 3 mm.

7. The analyzer using plasma according to claim 1, wherein said analyzing unit performs mass analysis.

8. The analyzer using plasma according to claim 1, wherein said analyzing unit performs emission light analysis.

9. The analyzer using plasma according to claim 1, wherein at least a portion of said introducing passage in the range of 1.5 mm to 3.0 mm from an end surface of the plasma side is designed so as to have a proper heat resistant structure.

10. The analyzer using plasma according to claim 1, wherein said introducing passage is constructed so as to essentially withstand a temperature corresponding to approximately 1300 W.

11. An interface for an analyzer using plasma comprising:

a plasma generator;

an introducing passage for supplying a sample to said plasma;

wherein at least a portion of said introducing passage in a plasma side is constructed so as to have a withstanding temperature higher than a withstanding temperature of a portion of said introducing passage in an inlet side;

a thermal stress moderating member disposed between the portion of said introducing passage having the higher withstanding temperature and the other portion of said introducing passage; and an output unit for outputting said supplied sample to said plasma.

12. An analysis method using plasma comprising the steps of:

generating plasma;

analyzing a sample by supplying said sample to said plasma through an introducing passage setting a portion of said introducing passage in a plasma side to a withstanding temperature higher than a withstanding temperature of a portion of said introducing passage in an inlet side; and inserting a thermal stress modulating member between the portion of said introducing passage having the higher withstanding temperature and the other portion of said introducing passage.

* * * * *

UNITED STATES PATENT AND TRADEMARK OFFICE
CERTIFICATE OF CORRECTION

PATENT NO. : 5,763,877
DATED : 9 June 1998
INVENTOR(S) : KonosukeOISHI et al.

It is certified that error appears in the above-identified patent and that said Letters Patent is hereby corrected as shown below:

| Column | Line | |
|--------|------|---|
| 2 | 4 | After "improved." delete "dr". |

Signed and Sealed this

Eleventh Day of May, 1999

Attest:

Q. TODD DICKINSON

Attesting Officer    Acting Commissioner of Patents and Trademarks